(12) United States Patent
Mauchan et al.

(10) Patent No.: US 6,641,782 B1
(45) Date of Patent: Nov. 4, 2003

(54) APPARATUS FOR PERFORMING DIAGNOSTIC TESTING

(75) Inventors: Donald E. Mauchan, Marlboro, MA (US); Komandoor E. Achyuthan, Oklahoma City, OK (US); James R. Appleman, Edmond, OK (US)

(73) Assignee: Polaroid Corporation, Waltham, MA (US)

( * ) Notice: Subject to any disclaimer, the term of this patent is extended or adjusted under 35 U.S.C. 154(b) by 430 days.

(21) Appl. No.: 09/713,705

(22) Filed: Nov. 15, 2000

(51) Int. Cl.[7] .............................................. G01N 21/76
(52) U.S. Cl. ......................................... 422/52; 422/102
(58) Field of Search ................... 422/52, 102; 436/172, 436/165; 250/361 C

(56) References Cited

U.S. PATENT DOCUMENTS

| | | | |
|---|---|---|---|
| 3,390,962 A | 7/1968 | Goldsmith .................... 23/253 |
| 3,415,361 A | 12/1968 | Adams, Jr. et al. ........... 206/47 |
| 3,680,967 A | 8/1972 | Engelhardt .................. 356/246 |
| 3,715,189 A | * 2/1973 | Nighohossian et al. ....... 422/61 |
| 3,788,205 A | 1/1974 | Pasieka et al. ................. 95/93 |
| 3,848,579 A | * 11/1974 | Villa-Real ................... 600/577 |
| 3,865,548 A | 2/1975 | Padawer .................... 23/230 |
| 4,111,754 A | 9/1978 | Park ........................... 195/127 |
| 4,233,029 A | 11/1980 | Columbus ................... 23/230 |
| 4,254,083 A | 3/1981 | Columbus ................... 422/55 |
| 4,264,560 A | 4/1981 | Natelson ..................... 422/58 |
| 4,271,119 A | 6/1981 | Columbus ................... 422/50 |
| 4,302,313 A | 11/1981 | Columbus ............... 204/195 R |
| 4,310,399 A | 1/1982 | Columbus ............... 204/195 R |
| 4,323,536 A | 4/1982 | Columbus .................... 422/56 |
| 4,371,498 A | 2/1983 | Scordato et al. ............ 422/102 |
| 4,396,579 A | 8/1983 | Schroeder et al. ............ 422/52 |
| 4,413,407 A | 11/1983 | Columbus .................... 29/825 |
| 4,426,451 A | 1/1984 | Columbus ................... 436/518 |
| 4,439,526 A | 3/1984 | Columbus ................... 436/180 |
| 4,510,393 A | 4/1985 | Sell et al. .................... 250/475 |
| 4,549,952 A | 10/1985 | Columbus ................... 204/416 |
| 4,587,221 A | 5/1986 | Cais et al. ................... 436/500 |
| 4,608,231 A | 8/1986 | Witty et al. ................... 422/61 |
| 4,675,299 A | 6/1987 | Witty et al. ................. 436/165 |
| 4,757,004 A | 7/1988 | Houts et al. ................... 435/7 |
| 4,772,453 A | 9/1988 | Lisenbee ..................... 422/52 |
| 4,797,259 A | 1/1989 | Matkovich et al. ......... 422/101 |
| 4,833,087 A | 5/1989 | Hinckley .................... 435/287 |
| 4,863,689 A | 9/1989 | Leong et al. ................. 422/52 |
| 4,906,439 A | 3/1990 | Grenner ...................... 422/56 |
| 4,918,025 A | 4/1990 | Grenner ..................... 436/165 |
| 4,948,564 A | 8/1990 | Root et al. .................. 422/101 |
| 4,948,975 A | 8/1990 | Erwin et al. ................. 250/361 |
| 4,959,324 A | 9/1990 | Ramel et al. ............... 436/169 |
| 4,973,549 A | 11/1990 | Khanna et al. ............... 435/11 |
| 4,978,502 A | 12/1990 | Dole et al. ................... 422/58 |
| 4,985,631 A | 1/1991 | Wannlund et al. .......... 250/361 |
| 4,987,085 A | 1/1991 | Allen et al. ................. 324/407 |
| 5,011,663 A | 4/1991 | Innocenti .................... 422/102 |
| 5,035,866 A | 7/1991 | Wannlund .................. 422/102 |

(List continued on next page.)

*Primary Examiner*—Jeffrey Snay

(57) ABSTRACT

The present invention relates generally to diagnostic assay systems and methods thereof that are capable of conducting and recording assays in a simple and reliable manner.

3 Claims, 1 Drawing Sheet

U.S. PATENT DOCUMENTS

| | | | |
|---|---|---|---|
| 5,063,090 A | 11/1991 | Wannlund | 427/384 |
| 5,073,484 A | 12/1991 | Swanson et al. | 435/7.92 |
| 5,075,077 A | 12/1991 | Durley, III et al. | 422/56 |
| 5,093,268 A | 3/1992 | Leventis et al. | 436/172 |
| 5,098,661 A | 3/1992 | Froehlich et al. | 422/102 |
| 5,100,621 A | 3/1992 | Berke et al. | 422/61 |
| 5,132,086 A | 7/1992 | Allen et al. | 422/56 |
| 5,159,197 A | 10/1992 | Wannlund | 250/328 |
| 5,164,301 A | 11/1992 | Thompson et al. | 435/29 |
| 5,167,922 A | 12/1992 | Long | 422/58 |
| 5,188,965 A | 2/1993 | Wannlund | 436/165 |
| 5,219,762 A | 6/1993 | Katamine et al. | 436/518 |
| 5,244,630 A | 9/1993 | Khalil et al. | 422/52 |
| 5,319,436 A | 6/1994 | Manns et al. | 356/246 |
| 5,332,549 A | 7/1994 | MacIndoe, Jr. | 422/63 |
| 5,355,215 A | 10/1994 | Schroeder et al. | 356/317 |
| 5,411,893 A | 5/1995 | Eden et al. | 436/165 |
| 5,418,171 A | 5/1995 | Kimura et al. | 436/518 |
| 5,441,894 A | 8/1995 | Coleman et al. | 436/518 |
| 5,457,527 A | 10/1995 | Manns et al. | 356/246 |
| 5,460,778 A | 10/1995 | Macindoe, Jr. | 422/63 |
| 5,482,839 A | 1/1996 | Ashihara et al. | 435/7.9 |
| 5,552,276 A | 9/1996 | Mochida et al. | 435/6 |
| 5,657,118 A | 8/1997 | Lee | 356/246 |
| 6,178,983 B1 * | 1/2001 | Culliinane et al. | 137/68.26 |
| 6,197,254 B1 * | 3/2001 | Silver et al. | 422/52 |
| 6,251,660 B1 * | 6/2001 | Muir et al. | 435/287.2 |
| 6,277,646 B1 * | 8/2001 | Guirguis et al. | 436/165 |
| 6,426,230 B1 * | 7/2002 | Feistel | 436/165 |

* cited by examiner

APPARATUS FOR PERFORMING DIAGNOSTIC TESTING

CROSS-REFERENCE TO RELATED APPLICATION

The present application is related to copending patent application Ser. No. 09/417,297 filed Oct. 13, 1999 and is related to copending U.S. non-provisional patent application Ser. No. 09/412,845 filed on Oct. 6, 1999 and entitled "Diagnostic Assay System and Method; as well as patent application filed on even date herewith.

BACKGROUND OF THE INVENTION

The present invention relates generally to diagnostic assay systems and methods thereof that are capable of conducting and recording assays in a simple and reliable manner.

A wide variety of systems and approaches exist which allow the occurrence and recording of luminescent reactions, such as of the chemiluminescent, or fluorescent type for qualitative and quantitative results. One class of analytical instruments typically used in this field is referred to as luminometers. Luminometers conduct and record luminescent reactions generated, for instance, by a biological test fluid sample that contains a reagent of interest, such as an analyte, and a reagent in an assay element. Examples of these approaches include single-sample luminometers fitted with photographic multipliers; single-sample luminometers fitted with solid-state detectors; multiple sample luminometers; automatic luminometers with imaging systems based on CCD cameras; and photographic camera type luminometers. Some of the foregoing devices using photographic films of the conventional and self-developing type for recording luminescent activity are described in, for example, in U.S. Pat. Nos.: 4,863,689; 5,035,866; and, 5,188,965. Heretofore known prior art tends to be limited in a number of ways, such as being expensive due to the relatively expensive electronics required, training of personnel required because of their relatively complicated nature, and being relatively cumbersome in use and expensive in construction.

In addition, the prior art contains many devices that deliver a solution containing an analyte of interest to a testing solution for generating a luminescent read-out signal that indicates the presence of an analyte of interest. It is important in conducting these assays for the solution containing such an analyte to be delivered to a testing solution in a manner that enhances the reliability of the testing. One known testing device is commercially available from Biotrace, Inc., Plainsboro, N.J. that uses a pick-up device or swab having testing rings that swipe a surface to be tested. The ampoule includes a generally hollow tubular housing for slidably receiving the pickup device. The ampoule is transparent, and has an open end portion that is adapted to receive the sample pick-up, and a closed end portion that is transparent whereby luminescent activity can form a latent image on a recording film. A sealing membrane is located generally transversely to the ampoule housing to define a chamber or reservoir with the closed end portion to sealingly accommodate an assay fluid therein. The sealing membrane is made of a thin-walled metallic material that is impervious to fluid and ambient atmosphere. The sealing membrane is adapted to be punctured by the sample pick-up device when the latter is inserted by an operator therethrough. The assay fluid can be one that generates a chemiluminescent signal in response to a reagent, such as ATP (Adenosine Triphosphate) being present on the sampling rings. ATP is used as an indicator of the presence of organic debris, such as microorganisms. The sample pick-up device includes a handle, a stem, and a plurality of laterally extending sampling rings. The sampling rings are used to engage a surface to be tested for microorganisms. A user merely rubs the rings against a surface to be tested, for instance, a food preparation surface and inserts the sampling ring into and through the membrane, whereupon the rings are immersed into the assay fluid. If ATP is present, in significant amounts on the sampling rings, it will react with the reagent in the fluid and generate a luminescent read-out signal that is recordable on the film.

Despite the existence of a wide variety of known diagnostic luminescent type testing systems and approaches, however, it is, nevertheless, desired to improve upon the overall ease, versatility, and reliability of such systems and their testing procedures, as well as reduce overall costs associated with their construction and use.

SUMMARY OF THE INVENTION

In accordance with the present invention provision is made for an improved device for implementing chemiluminescent tests in a robust manner. Provision is made for a chemical implementation device comprising: a housing assembly including at least a pair of containers each of which is adapted to contain a fluid; a fluid impervious membrane sealing one of the pair of containers from the other of the pair of containers, thereby keeping fluids in each of the containers separate; and, a penetrating assembly mounted for movement in the housing assembly and being adapted to engage and penetrate the sealing membrane upon movement in response to a force being applied thereto for allowing fluid in the one container to mix with fluid in the other container under pressure; the housing assembly including at least a segment thereof that is transparent to a read-out signal generated in response to a reaction of the mixing fluids.

In an illustrated preferred embodiment, the sealing membrane includes a main body having at least one flap integral therewith and a weakened frangible portion of the membrane surrounding a peripheral portion of the flap such that the penetrating assembly can force separation of the flap from the body along the frangible portion to thereby facilitate flow of fluid from the one chamber to the other chamber.

In another illustrated preferred embodiment, the housing assembly includes two housing portions, each one of which defines a respective one of the chambers, wherein one of the two housing portions is removably coupled to the other portion for allowing separation and rejoining of the housing portions.

In still another illustrated preferred embodiment, the penetrating assembly includes a piston portion that is in sliding engagement with an internal wall of one of the chambers and is movable with the penetrating element for forcing fluid in the one chamber into the other chamber.

In yet still another illustrated embodiment, the piston portion has a frictional fit with the internal wall that is sufficient in magnitude to resist piston movement until application thereto of a reselected force.

In an illustrated and preferred embodiment of the present invention, a chemiluminescent test implementing device is provided that is a capable of storing testing solutions in separable chambers until implementation of a particular testing procedure is commenced. Included in the implementing device is a container comprising at least two adjoining chambers, each one of which is adapted to contain an appropriate solution. For sealingly separating these solutions prior to commencing a testing procedure, provision is made for a sealing assembly. When the testing is commenced the seal is opened by a device that penetrates the seal as well as induces in intimate or vortex-like mixing action for allowing the separated test fluids to be intimately mixed. Accordingly, an opportunity exists for a more robust chemiluminescent reaction occurring. A window at the bottom of the mixing chamber is in juxtaposed relationship to a film unit and allows for a chemiluminescent reaction to be recorded. Opening the sealing assembly and inducing the vortex-like mixing in the mixing chamber occurs responsive to penetration of the seal by a member that is advanced by forces transmitted thereto by a force-applying member. The force applying member can be activated such as when the operator closes a cover in a testing device. In addition, the container allows one of the chambers to be separated from the housing assembly to allow an operator to insert a sampling device, such as a swab containing microorganisms, into the fluid retained in the chamber. The chamber is then rejoined to the container in preparation of the seal being opened by the penetrating device upon application of the penetrating force, thereby allowing the fluids in both chambers to be mixed so as to be capable of generating a luminescent read-out signal recordable on an image recording medium. In a further illustrated embodiment, the penetrating device includes a piston which upon application of the penetrating force acts to force testing fluid under pressure from the one chamber to the mixing chamber under a vortex-like mixing action so as to better ensure the mixing of the solutions.

The above and other objects and features of the present invention will become apparent when reading the following description taken conjunction with the accompanying drawings wherein like parts are indicated by like reference numerals throughout the several views.

DETAILED DESCRIPTION

Figure 1:
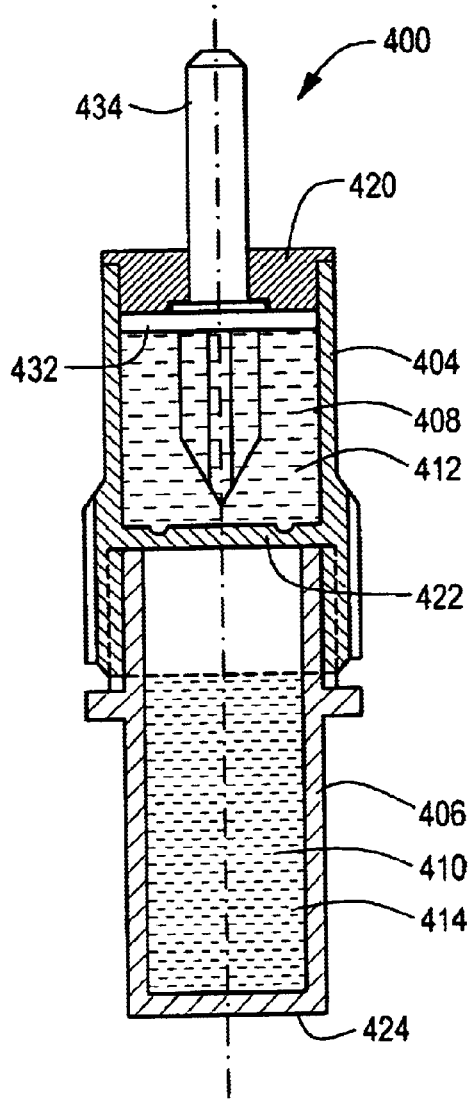
FIG. 1 is a cross-sectional view of a novel chemical implementation device of the present invention.
Figure 2:
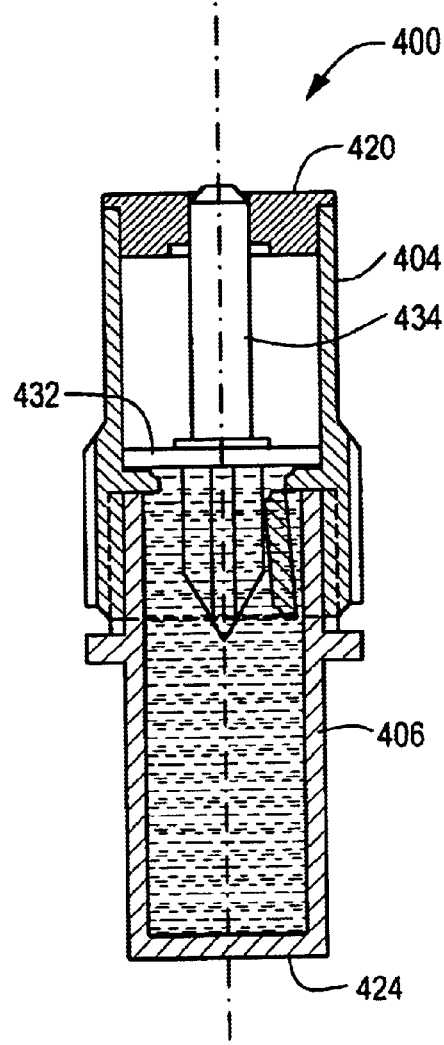
FIG. 2 is a view similar to that of FIG. 1, but with the chemical implementation device illustrated in an operative mode; and, FIG. 3 is a cross-sectional view taken along section line 3—3 appearing in FIG. 1.
Figure 3:
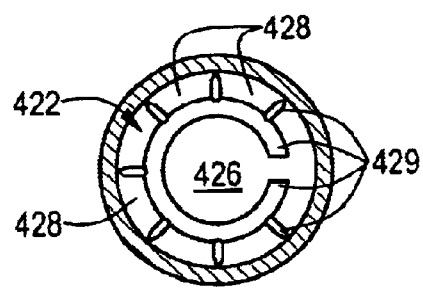

FIGS. 1–3 illustrate a preferred embodiment of the present invention, wherein a chemiluminescent implementing device 400 is provided for use in selectively storing, transporting fluids to be used in a diagnostic assay test device. The implementing device includes a transportable vial 402 comprising a pair of generally coaxially aligned and separable upper and lower fluid containers 404 and 406 that are releaseably coupled together as by a threaded connection for reasons that will be explained. Both the upper and lower containers 404, 406 are made of suitable plastic materials which are inert to the assay compounds. Such materials include polyethylene, polypropylene, polystyrene, polycarbonate, SUBS or some other suitable materials. The containers 404, 406 as constructed define fluid chambers 408, 410; respectively, that are particularly adapted for housing the testing solutions or fluids 412, 414. The testing fluids 412, 414 are any suitable type depending on the type of chemiluminescent testing to be conducted and hence do not, per se, form an aspect of the present invention. Samples to be assayed include biological fluids, microorganisms and viruses as well as non-biological fluids. The chamber 408 has a plastic sealing plug 420 closing its upper end and a fluid impervious sealing membrane 422 closing its lower end. The sealing membrane 422 serves to separate the fluids 412, 414 until the sealing is broken in a manner to be described and is inert to the fluids that it separates. The lower chamber 406 has a bottom wall 424 that defines a transparent window allowing optical communication of a chemiluminescent reaction within the chamber to a film unit (not shown) disposed in juxtaposition thereto. The sidewalls defining the chamber 410 can be opaque or transparent.

For opening the membrane 422, a plunger assembly 430 is provided which includes a piston 432 being in slidable engagement with the internal walls of the upper container. A stem 434 protrudes upwardly from the piston 432 and sealingly through an opening in the plug 420. The plug can be disassembled from the piston and stem. Furthermore, the plug 420 along with the piston 432 and stem 434 can be removed from the upper chamber so that the fluid 412 can first be filled into the upper chamber 404 and then resealed using the plug and piston and stem. The plug dimensions are such that they form a very tight and snug fit around the inner walls of the upper chamber 404 and along with the piston 432/stem 434 assembly, prevents the accidental leaking of fluid from the upper chamber 404. A force is applied to the stem 434 as by closing a door of a testing device (not shown) to move the piston and displace the fluid 412 for reasons to be described. The testing device is described in copending U.S. patent application Ser. No. 09/713,668 and a description thereof is incorporated herein by reference and made a part hereof. In this embodiment, the piston 432 has a sufficient friction fit with the upper chamber walls for resisting movement if ordinary manual forces are applied to the stem, such as by a user handling the device. The friction forces are overcome after a predetermined force is applied thereto, such as by the closing the door of the testing device noted above. In any event, the friction should be such as to prevent inadvertent piston movement while allowing intended piston movement for preventing premature mixing of the fluids. A fluted penetrating element 436 is centrally attached to the piston 432 and has a configuration such as illustrated for engaging and puncturing the membrane 422 upon displacement of the piston towards the membrane. The penetrating element 436 is adapted to puncture the membrane as the element is being displaced while the piston itself develops sufficient pressure on the fluid 412 to further force the latter into the chamber 410 as well as create a vortex-like mixing action with the fluid 414 in the lower fluid chamber. The pressure generated by the piston is sufficient to overcome forces, such as surface tension, that might inhibit the desired fluid flow of fluid 412 into mixing with the fluid 414. Accordingly, the action of the piston generates a robust and intimate mixing action, thereby better ensuring a proper mixing action for generating a chemiluminescent reaction. It will be understood that the type of luminescent activity can be of the chemiluminescent, fluorescence, and infrared types as well as other signals that are recordable on an image recording material.

Reference is made to FIG. 3 for illustrating an improved membrane construction that further enhances the intimate mixing reaction desired. In particular, the membrane 422 has a thin-walled and flexible body that is inert to the fluids it is to be in contact. The membrane 422 can be made from a variety materials and, in this preferred embodiment is made of polypropylene. Integrally formed in the membrane 422 is a plurality of radially inwardly directed flap portions 426 generally extending about the periphery of the membrane as illustrated as well as a larger central flap 428. The flaps 426, 428 are constructed to bend individually relative to each other and the remainder of the membrane about their proximal ends relative to each other for improving fluid flow in response to displacement of the piston and the penetrating element. Towards this end, the membrane 422 preferably has a general thickness in the order of about 0.005 inches and frangible grooves 429 having a thickness of about 0.003 inches. The frangible grooves 429 define weakened areas substantially about the periphery of each of the flaps. When the penetrating element engages the membrane, it engages the central flap 428 and urges the latter to be torn along the grooves 429 from the membrane and bend about its proximal end. Further inward movement of the penetrating element causes the other grooves to be torn thereby allowing the flaps 426 to move independently of each other and the remainder of the membrane. Accordingly, the flow of fluid 412 is even less inhibited by the membrane. It will be appreciated that by having the flaps flex about their proximal end they do not break off and drop to the bottom of the lower chamber. As a result the flaps might otherwise inhibit the desired mixing action as well as possibly occlude light from the bottom wall, thereby diminishing sensitivity of the diagnostic test.

In use, an operator would separate the containers by unfastening them. The operator would take a test sample, such as by swabbing a patient's throat, and insert the swab into the fluid 414. After removing the swab from the fluid, the operator reconnects the two containers. Force is applied to the penetrating assembly as by the device disclosed in copending patent application, Ser. No. 09/713,668. Force is applied to the stem 434 so as to move the piston 432 and the penetrating element 436, whereby the latter punctures the membrane and allows fluid under pressure from the piston to flow into the upper chamber to intimately mix with fluid in the lower chamber under vortex-like conditions. If a luminescent reaction occurs, such will be transmitted to a device, such as film through the transparent wall. Because of the self-contained nature of the foregoing device, the entire device can be safely disposed of as one unit thereby making decontamination of potentially biohazardous materials easier, without the operator having to open the device or unit. It will also be realized that the penetrated membrane prevents reuse.

While there have been described what at present is considered to the preferred embodiments of the present invention, it will be readily apparent to those skilled in the art that various changes may be made therein without departing from the invention, and it is intended in the claims to cover such changes and modifications as fall within the true spirit and scope of the invention.

What is claimed is:

1. A chemiluminescent reaction implementation device comprising: a housing assembly including at least a pair of containers each of which is adapted to contain a different fluid, said different fluids being of the types which may produce a chemiluminescent reaction when mixed together; a fluid impervious membrane sealing one of the pair of containers from the other of the pair of containers, thereby keeping said different fluids in each of the containers separate; and, a penetrating assembly mounted for movement in the housing assembly and being adapted to engage and penetrate the sealing membrane upon movement in response to a force being applied thereto for forcing fluid in the one container to mix with fluid in the other container under pressure while creating a vortex-like mixing action to enhance generation of a chemiluminescent reaction; the housing assembly including at least a segment thereof that is transparent to a light-emitting read-out signal generated in response to a chemiluminescent reaction of the mixing fluids; and the pair of containers are removably coupled to each other to allow separation and rejoining thereof by an operator and wherein said sealing membrane has a plurality of integrally formed and radially inwardly directed flap portions generally extending about the periphery of said membrane as well as a larger central flap, said membrane further including frangible grooves defining weakened areas substantially about the periphery of each of said flaps whereby the penetrating assembly causes the membrane to be torn along the grooves and bends the flaps at proximal ends thereof so that the flaps move independently of each other and the remainder of the membrane for further improving fluid flow and mixing of the different fluids.

2. The device of claim 1 wherein each of the flaps bend about a proximal end thereof and remain attached to the membrane after the membrane is penetrated, thereby preventing the flaps from possibly occluding the transparent segment whereby signals from a chemiluminescent reaction would be diminished.

3. The device of claim 1 wherein the penetrating assembly includes a piston portion that is in sliding engagement with an internal wall of one of the containers is movable with the penetrating element for forcing fluid in one container to the other container wherein the piston portion has a frictional fit with the internal wall which is sufficient in magnitude to resist movement thereof until application of a preselected force thereto, and wherein said preselected force is greater than ordinary manual forces applied to the piston potion when a users routinely handles the implementation device.

\* \* \* \* \*